(12) United States Patent
Levin et al.

(10) Patent No.: US 7,395,111 B2
(45) Date of Patent: Jul. 1, 2008

(54) TRANSDERMAL DELIVERY SYSTEM FOR WATER INSOLUBLE DRUGS

(75) Inventors: Galit Levin, Nordiya (IL); Meir Stern, Rehovot (IL); Dorit Daniel, Ra'anana (IL)

(73) Assignee: TransPharma Medical Ltd., Lod (IL)

( * ) Notice: Subject to any disclaimer, the term of this patent is extended or adjusted under 35 U.S.C. 154(b) by 166 days.

(21) Appl. No.: 11/116,056

(22) Filed: Apr. 27, 2005

(65) Prior Publication Data
US 2005/0287217 A1 Dec. 29, 2005

Related U.S. Application Data

(63) Continuation of application No. PCT/IL03/00901, filed on Oct. 30, 2003.

(30) Foreign Application Priority Data
Oct. 31, 2002 (IL) .......................... 152575

(51) Int. Cl.
*A61N 1/30* (2006.01)
(52) U.S. Cl. .......................... 604/20; 604/501
(58) Field of Classification Search ............. 604/19–21, 604/501
See application file for complete search history.

(56) References Cited

U.S. PATENT DOCUMENTS

| | | | | |
|---|---|---|---|---|
| 3,964,482 | A | | 6/1976 | Gerstel et al. ............... 128/260 |
| 4,559,222 | A | | 12/1985 | Enscore et al. ............... 424/28 |
| 4,668,232 | A | | 5/1987 | Cordes et al. ............... 604/897 |
| 4,704,282 | A | | 11/1987 | Campbell et al. ............ 424/449 |
| 4,727,064 | A | * | 2/1988 | Pitha ........................... 514/58 |
| 4,867,982 | A | | 9/1989 | Campbell et al. ............ 424/449 |
| 4,978,532 | A | * | 12/1990 | El-Rashidy ................. 424/448 |
| 5,019,034 | A | | 5/1991 | Weaver et al. ................. 604/20 |
| 5,068,226 | A | * | 11/1991 | Weinshenker et al. ......... 514/58 |
| 5,120,546 | A | * | 6/1992 | Hansen et al. .............. 424/449 |
| 5,152,997 | A | | 10/1992 | Ebert et al. ................. 424/449 |
| 5,158,537 | A | | 10/1992 | Haak et al. .................... 604/20 |
| 5,203,768 | A | * | 4/1993 | Haak et al. .................... 604/20 |

(Continued)

FOREIGN PATENT DOCUMENTS

WO   WO 95/03764   2/1995

(Continued)

OTHER PUBLICATIONS

Yuri A. Chizmadzhev et al., "Electrical Properties of Skin at Moderate Voltages: Contribution of Appendageal Macropores", Biophysical Journal, vol. 74, pp. 843-856 (1998).

(Continued)

*Primary Examiner*—Sharon E. Kennedy
(74) *Attorney, Agent, or Firm*—Winston & Strawn LLP

(57) ABSTRACT

The present invention provides a system for transdermal delivery of water insoluble drugs and methods using the same. The system includes a pharmaceutical composition of a water insoluble drug and a carrier molecule that enhances the solubility of the drug in aqueous solution, a medical patch containing the same and an apparatus that generates hydrophilic micro-channels in an area of skin of a subject using the composition or patch. The system preferably avoids the use of penetration enhancers and is particularly useful for transdermal delivery of steroids.

39 Claims, 10 Drawing Sheets

U.S. PATENT DOCUMENTS

| | | | | |
|---|---|---|---|---|
| 5,230,898 | A | 7/1993 | Hortsmann et al. | 424/449 |
| 5,320,597 | A | 6/1994 | Sage, Jr. et al. | 604/20 |
| 5,376,645 | A | 12/1994 | Stella et al. | 514/58 |
| 5,421,816 | A * | 6/1995 | Lipkovker | 604/20 |
| 5,445,609 | A | 8/1995 | Lattin et al. | 604/20 |
| 5,460,820 | A | 10/1995 | Ebert et al. | 424/449 |
| 5,618,265 | A | 4/1997 | Myers et al. | 604/20 |
| 5,622,944 | A | 4/1997 | Hale et al. | 514/181 |
| 5,685,837 | A | 11/1997 | Hortsmann | 604/20 |
| 5,807,306 | A | 9/1998 | Shapland et al. | 604/21 |
| 5,824,668 | A | 10/1998 | Rubinfeld et al. | 514/170 |
| 5,840,327 | A | 11/1998 | Gale et al. | 424/448 |
| 5,874,418 | A | 2/1999 | Stella et al. | 514/58 |
| 5,885,211 | A | 3/1999 | Eppstein et al. | 600/309 |
| 5,928,571 | A | 7/1999 | Chan | |
| 5,944,685 | A | 8/1999 | Muroki | 604/20 |
| 5,983,130 | A | 11/1999 | Phipps et al. | 604/20 |
| 5,983,135 | A | 11/1999 | Avrahami | 604/20 |
| 5,989,586 | A | 11/1999 | Hsu et al. | 424/449 |
| 5,993,435 | A | 11/1999 | Haak et al. | 604/501 |
| 6,004,578 | A | 12/1999 | Lee et al. | 424/448 |
| 6,022,316 | A | 2/2000 | Eppstein et al. | 600/309 |
| 6,046,177 | A | 4/2000 | Stella et al. | 514/58 |
| 6,050,988 | A | 4/2000 | Zuck | 604/890.1 |
| 6,083,196 | A | 7/2000 | Trautman et al. | 604/46 |
| 6,132,760 | A | 10/2000 | Hedenstrom et al. | 424/448 |
| 6,142,939 | A | 11/2000 | Eppstein et al. | 600/309 |
| 6,148,232 | A | 11/2000 | Avrahami | 604/20 |
| 6,169,920 | B1 | 1/2001 | Haak et al. | 604/20 |
| 6,173,202 | B1 | 1/2001 | Eppstein | 600/309 |
| 6,219,577 | B1 | 4/2001 | Brown, III et al. | 604/20 |
| 6,317,629 | B1 | 11/2001 | Haak et al. | 604/20 |
| 6,522,918 | B1 | 2/2003 | Crisp et al. | 604/20 |
| 6,532,386 | B2 * | 3/2003 | Sun et al. | 604/20 |
| 6,597,946 | B2 | 7/2003 | Avrahami et al. | 604/20 |
| 6,611,706 | B2 | 8/2003 | Avrahami et al. | 604/20 |
| 6,622,037 | B2 | 9/2003 | Kasano | 604/20 |
| 6,662,044 | B2 | 12/2003 | Crawford et al. | 604/20 |
| 6,678,554 | B1 * | 1/2004 | Sun et al. | 604/20 |
| 2002/0010414 | A1 | 1/2002 | Coston et al. | 604/20 |
| 2002/0038101 | A1 | 3/2002 | Avrahami et al. | 604/20 |
| 2002/0058936 | A1 | 5/2002 | Avrahami et al. | 604/20 |
| 2003/0139731 | A1 | 7/2003 | Marchitto et al. | 604/890.1 |
| 2003/0204163 | A1 | 10/2003 | Marchitto et al. | 604/65 |
| 2004/0059282 | A1 | 3/2004 | Flock et al. | 604/20 |

FOREIGN PATENT DOCUMENTS

| | | |
|---|---|---|
| WO | WO 96/16659 | 6/1996 |
| WO | WO 97/07734 | 3/1997 |
| WO | WO 97/24148 | 7/1997 |
| WO | WO 98/37871 | 9/1998 |
| WO | WO 98/53815 | 12/1998 |
| WO | WO 00/47208 | 8/2000 |
| WO | WO 00/76522 A1 | 12/2000 |
| WO | WO 01/85234 A2 | 11/2001 |
| WO | WO 02/17927 A1 | 3/2002 |
| WO | WO 02/085451 A2 | 10/2002 |
| WO | WO 02/092163 A2 | 11/2002 |

OTHER PUBLICATIONS

Yuri A. Chizmadzhev et al., Electrical Properties of Skin at Moderate Voltages: Contribution of Appendageal Macropores, Biophysical Journal, vol. 74, Feb. 1998, pp. 843-856.

US 6,214,374, 04/2001, Schmirler et al. (withdrawn)

* cited by examiner

TRANSDERMAL DELIVERY SYSTEM FOR WATER INSOLUBLE DRUGS

CROSS-REFERENCE TO RELATED APPLICATION

This application is a continuation of International application PCT/IL2003/000901 filed Oct. 30, 2003, the entire content of which is expressly incorporated herein by reference thereto.

FIELD OF THE INVENTION

The present invention relates to the field of transdermal drug delivery, more particularly to a transdermal delivery system for administration of water insoluble drugs, such as steroids, in conjunction with an apparatus that operates by generating micro-channels in the skin of a subject.

BACKGROUND OF THE INVENTION

Transdermal drug delivery is an attractive concept as such means may offer a convenient and comfortable mode of delivery. The variable rates of absorption and metabolism encountered in oral administration are avoided, together with eliminating adverse effects such as gastro-intestinal irritation; it is a noninvasive method, and it may provide superior control of blood concentration of a particular drug over time.

However, skin is a complex structure that functions as a barrier to ingress of foreign substances into the body. Molecules moving from the environment into and through intact skin must first penetrate the stratum corneum, which presents the primary barrier to absorption of topical compositions or transdermally administered drugs, especially for oil-insoluble and ionized salt forms of drugs.

A number of different methods have been developed for transdermal drug delivery, enabling the administration of a variety of drugs. One approach includes formulations of drugs as to enable their delivery through the skin, including development of number of skin penetration enhancing agents, or "permeation enhancers", to increase skin permeability. The formulated drugs may be applied to the skin in the forms of patches, films, or matrices of various compositions. Another approach includes non-chemical modes for facilitating transdermal delivery, e.g. the use of iontophoresis, electroporation or sonophoresis.

Transdermal Delivery Apparatus

Electrotransport or iontophoretic drug delivery devices have been disclosed as being useful for the delivery of drugs for which it is anticipated that transdermal delivery would be advantageous. U.S. Pat. Nos. 6,169,920 and 6,317,629 to Alza for example disclose iontophoretic drug delivery apparatus, and U.S. Pat. No. 5,983,130 to Alza discloses an electrotransport agent delivery method and apparatus suitable for ionizable drugs.

Electroporation is also well known in the art as a method to increase pore size by application of an electric field. Electroporation is disclosed as a means for transiently decreasing the electrical resistance of the stratum corneum and increasing the transdermal flux of small molecules by applying an electric field to increase the size of existing pores (Chizmadzhev et al., Biophysics Journal, 1998, 74 (2), 843-856).

U.S. Pat. No. 5,019,034 to Weaver et al. describes apparatus for applying high voltage, short duration electrical pulses on the skin to produce electroporation.

WO 97/07734 to Eppstein et al. discloses thermal ablation of the stratum corneum using an electrically resistive element in contact with the stratum corneum, such that a high current through the element causes a general heating of tissue in its vicinity, most particularly the stratum corneum 10-50 micron thick outermost layer of the skin.

U.S. Pat. Nos. 5,885,211, 6,022,316, 6,142,939 and 6,173, 202 to Eppstein et al., which are incorporated herein by reference, describe methods for forming micropores in the stratum corneum by heating tissue-bound water above the vapor point with a heat-conducting element, so as to enhance transdermal transport of an analyte or active substance. Further enhancement techniques include the use of sonic energy, pressure, and chemical enhancers.

U.S. Pat. No. 3,964,482 to Gerstel, U.S. Pat. No. 6,050,988 to Zuck, and U.S. Pat. No. 6,083,196 to Trautman et al. describe other apparatus and methods for facilitating transdermal movement of a substance.

U.S. Pat. No. 6,148,232 to Avrahami, which is incorporated herein in its entirety by reference, describes apparatus for applying electrodes at respective points on skin of a subject and applying electrical energy of radio frequency (RF) between two or more of the electrodes to cause ablation of the stratum corneum primarily in an area intermediate the respective points, forming micro-channels. Various techniques for limiting ablation to the stratum corneum are described, including spacing of the electrodes and monitoring the electrical resistance of skin between adjacent electrodes.

The apparatus of the type disclosed in U.S. Pat. No. 6,148, 232 and continuations thereto (U.S. Pat. Nos. 5,983,135; 6,597,946; and 6,611,706, and International Patent Application Nos. WO01/85234; WO 02/085451; and WO 02/092163) is referred to hereinafter by the names ViaDerm or MicroDerm.

Transdermal Patches

There are two prevalent types of transdermal patch designs, namely the reservoir type where the drug is contained within a reservoir having a basal surface that is permeable to the drug, and a matrix type, where the drug is dispersed in a polymer layer affixed to the skin. Both types of device typically include a backing layer and a release liner layer that is removed prior to use. In an effort to increase skin permeability so that the drugs can be delivered in therapeutically effective amounts, it has been proposed to pretreat the skin with various chemicals or to concurrently deliver the drug in the presence of adjuvants known as "increasers" or "permeation enhancers" to increase the rate of permeation of the active ingredient. Various materials have been suggested for this purpose, as described for example in U.S. Pat. No. 6,004,578 to Lee at al., and references therein, which are incorporated herein by reference.

However, such permeation enhancers often cause problems such as irritation, sensitization, or severe inconvenience, and therefore the number of drugs that can be safely and effectively administered through skin remains limited.

Delivery of Water-Insoluble Drugs

Many powerful drug substances are insoluble in water, limiting the effectiveness of their use as therapeutic agents. One approach to enhance the solubility of such drugs in water is to form a reversible complex between the water insoluble drug and a carrier molecule; the characteristics of the carrier molecule are such that the carrier molecule and the reversible complex are soluble in water. Among the carrier molecules are amorphous cyclodextrins described, for example, in U.S. Pat. Nos. 5,134,127; 5,376,645; 5,874,418; and 6,046,177. The use of cyclodextrin and its derivatives as solubilizing agents for water insoluble drugs for oral, intranasal, or parenteral administration is disclosed.

Steroid compounds affect a large number of important physiological functions in humans, and natural as well as synthetic steroids and their derivatives are in use for therapeutic purposes. Methods of steroid administration depend both on the steroid and on the specific disorder. Many of the beneficial steroids that are administered therapeutically to patients are insoluble in water.

The steroid testosterone is the main androgenic hormone formed in the testes. Testosterone therapy is indicated for the treatment of male hypogonadism, and is also suggested for treatment of wasting conditions associated with AIDS and cancer, for treatment of osteoporosis, and for combination hormone replacement therapy for women and male fertility control.

Transdermal delivery of androgens, alone or in combination with estrogenic agents has been disclosed, for example, in U.S. Pat. Nos. 4,867,982; 5,460,820; 5,622,944; and 6,214,374; and in International Patent Application Nos. WO 95/03764; WO 97/24148; WO 98/37871; and WO 00/76522. Many of the cited patents disclose the use of various patches for the transdermal delivery of testosterone. One limitation in the use of such patches is the requirement for scrotal application, which presents problems of inconvenience to the patients (U.S. Pat. Nos. 4,704,282; and 5,840,327). Although non-scrotal application was also suggested (for example, U.S. Pat. Nos. 5,152,997; and 6,132,760), efficient delivery through skin requires the use of permeation enhancers, which by themselves may cause severe problems of irritation and sensitization. In addition, the size of suggested patches is, for small patches, at the range of 30 cm$^2$, while most frequently used patches are at a size range of 60 cm$^2$. Another limitation in the use of such patches is the inability to adequately control androgen serum concentrations and hence androgen bioavailability. Transdermal delivery of androgen formulated into gels was also suggested (e.g. WO 0217927); the main limitation of administering androgen by way of a gel is the resulted undesired contamination of other subjects being in a close contact with the subject in need.

The use of amorphous cyclodextrins for pharmaceutical formulation of steroids to enable therapeutic administration has been disclosed, but nowhere in the background art is it taught or suggested that these formulations are suitable for transdermal use.

The aforementioned U.S. Pat. No. 5,874,418 demonstrates the utility of a specific cyclodextrin derivative having 7 sulfoalkyl ether substituents, (SBE)7-β-cyclodextrin, for the preparation of sustained release formulation of a pharmacologically active agent, with testosterone serving as an example.

U.S. Pat. No. 5,824,668 discloses compositions including at least one 5β steroid and an amorphous cyclodextrin formulated for parenteral administration. International Patent application WO 96/16659 discloses stabilized suspension of corticosteroids with cyclodextrins useful for therapeutic treatment of the eye, ear and nose.

Thus, there is a recognized need for, and it will be highly advantageous to have compositions and methods for an efficient transdermal delivery of water-insoluble drugs in general, and water insoluble steroids in particular, which scarcely cause irritation and are applied to small skin areas.

SUMMARY OF THE INVENTION

It is an object of some aspects of the present invention to provide an effective system and methods for transdermal delivery of water insoluble drugs. More specifically, it is an object of the present invention to provide improved system and methods for transdermal delivery of steroids.

It is another object of some aspects of the present invention to provide a transdermal delivery system of water insoluble drugs that causes minimal irritation and sensitization of the skin area to which the drugs are applied.

It is yet another object of some aspects of the present invention to provide a transdermal delivery system of water insoluble drugs that achieves therapeutic blood concentrations of the drugs.

It is now disclosed that a system comprising: an apparatus capable of generating hydrophilic micro-channels in an area on the skin of a subject; and a medical patch comprising a water insoluble drug and a carrier molecule that enhances the solubility of the drug in aqueous solution, is capable of facilitating the transdermal delivery of the drug from the patch into the blood of the subject.

The combination of hydrophilic micro-channels and a patch comprising a water insoluble drug, which is formulated in a water-soluble formulation, enables achieving, for the first time, a substantial and efficient delivery of a water insoluble drug into the blood of a subject, while causing minimal irritation and sensitization to the skin.

The present invention also provides, for the first time, a medical patch of a water-insoluble drug wherein the drug is solubilized into an aqueous solution by a carrier molecule. The patch further comprises a hydrophilic polymer. It is now disclosed that use of such patch in combination with the apparatus of the invention provides an efficient means for slow transdermal delivery of a water insoluble drug without causing skin irritation.

According to a first aspect, the present invention provides a system for transdermal delivery of a water insoluble drug comprising: an apparatus for facilitating transdermal delivery of a drug through skin of a subject, said apparatus generates at least one micro-channel in an area on the skin of a subject; and a patch comprising a pharmaceutical composition comprising at least one water insoluble drug and at least one carrier molecule that enhances the solubility of the drug in aqueous solution.

Typically, water insoluble drug will have solubility in water of less than about 0.1-1 mg/ml at room temperature.

The term "micro-channel" as used herein refers to a pathway, generally extending from the surface of the skin through all or significant part of the stratum corneum, through which molecules can diffuse.

The compositions and methods of the present invention are suitable for use with many of the patches known in the art, though application of the drug with the system of the present invention has proven particularly effective.

According to one embodiment, the water-insoluble drug is selected from the group consisting of natural or synthetic anesthetics, analgesics, antagonists, antiadrenergic and antiarrhythmics, antibiotics, anticholinergic and cholinomimetic agents, anticonvulsant agents, antidepressants, anti-epileptics, antifungal and antiviral agents, anti-inflammatory agents, antimuscarinic and muscarinic agents, antineoplastic agents, antipsychotic agents, anxiolytics, hormones, hypnotics, immunosuppressive or immunoactive agents, neuroleptic agents, neuron blocking agents, antihypertensive agents, nutrients, sedatives, steroids, and derivatives thereof.

According to another embodiment, the steroid is androgen. According to a currently preferred embodiment, the androgen is testosterone.

According to another embodiment, the carrier molecule to be used is selected from the group consisting of α, β and γ cyclodextrins and derivatives thereof.

According to yet another embodiment, the carrier molecule is selected from the group of β-cyclodextrins. According to a currently preferred embodiment the carrier molecule is sulfobutyl ether-β-cyclodextrin.

According to another embodiment the pharmaceutical composition may further comprise one or more components known in the art, including but not limited to, water-soluble polysaccharides, hydrophilic polymers, diluents, colors, adhesives, preservatives, anti-oxidants, buffer agents and stabilizers. The pharmaceutical composition is devoid of penetration enhancers. The formulation can be in any suitable form, for example a solution, a powder, a gel, a hydrogel and the like.

According to some embodiments the present invention incorporates the techniques for creating micro-channels by inducing ablation of the stratum corneum, using RF electrical energy, including the apparatus referred to as ViaDerm or MicroDerm disclosed in one or more of the following: U.S. Pat. No. 6,148,232 to Avrahami; U.S. Pat. No. 5,983,135 to Avrahami; U.S. Pat. No. 6,597,946 to Avrahami et al.; U.S. Pat. No. 6,611,706 to Avrahami et al.; WO 01/85234; WO 02/085451; WO 02/092163; the contents of which is incorporated herein in its entirety by reference. It is however emphasized that although some preferred embodiments of the present invention relates to transdermal delivery obtained by ablating the skin by the aforementioned apparatus, substantially any method known in the art for generating channels in the skin of a subject may be used.

According to a certain embodiment of the invention, the system comprises an apparatus for facilitating transdermal delivery of a drug through skin of a subject, said apparatus comprising:
 a. an electrode cartridge, optionally removable, comprising at least one electrode, preferably a plurality of electrodes;
 b. a main unit comprising a control unit which is adapted to apply electrical energy to the electrode when the electrode is in vicinity of the skin, typically generating current flow or one or more sparks, enabling ablation of stratum corneum in an area beneath the electrode, thereby generating at least one micro-channel.

In another embodiment, the system of the invention generates a plurality of micro-channels, wherein the micro-channels are of uniform shape and dimensions.

According to another aspect, the present invention provides a medical patch comprising a pharmaceutical composition comprising at least one water-insoluble drug and at least one carrier molecule that enhances the solubility of the drug in aqueous solution.

According to one embodiment, the water-insoluble drug is selected from the group consisting of natural or synthetic anesthetics, analgesics, antagonists, antiadrenergic and antiarrhythmics, antibiotics, anticholinergic and cholinomimetic agents, anticonvulsant agents, antidepressants, anti-epileptics, antifungal and antiviral agents, anti-inflammatory agents, antimuscarinic and muscarinic agents, antineoplastic agents, antipsychotic agents, anxiolytics, hormones, hypnotics, immunosuppressive or immunoactive agents, neuroleptic agents, neuron blocking agents, antihypertensive agents, nutrients, sedatives, steroids, and derivatives thereof.

According to another embodiment, the steroid is androgen. According to a currently preferred embodiment, the androgen is testosterone.

According to yet another embodiment the carrier molecule to be used is selected from the group consisting of α, β, and s γ cyclodextrins and derivatives thereof.

According to another embodiment, the carrier molecule is selected from the group of β-cyclodextrins. According to one currently preferred embodiment the carrier molecule is sulfobutyl ether-β-cyclodextrin.

According to yet another embodiment the medical patch further comprises at least one layer selected from a backing layer, an adhesive, and a release liner.

According to yet another aspect the present invention provides a method for enhancing transdermal delivery of a water-insoluble drug, the method comprising the steps of:
 (i) generating of at least one micro-channel in a region of skin of a subject; and
 (ii) affixing a patch to the region of the skin in which the micro-channels are present, the patch comprises a pharmaceutical composition comprising at least one water-insoluble drug and at least one carrier molecule that enhances the solubility of the drug in aqueous solution.

According to another embodiment the present invention provides a method for enhancing transdermal delivery of a water-insoluble drug, the method comprising the steps of:
 (i) generating of at least one micro-channel in a region of skin of a subject; and
 (ii) affixing a patch to the region of the skin in which the micro-channels are present, the patch comprises a pharmaceutical composition comprising at least one water-insoluble drug and at least one carrier molecule that enhances the solubility of the drug in aqueous solution.
 (iii) achieving a therapeutic blood concentration of the drug.

The method of the invention achieves serum concentration of at least 1 ng/ml of water insoluble drug. Preferably, the serum concentration of at least 1 ng/ml of the water insoluble drug is maintained over a period of at least 12 hours, and more preferably for a period of at least 24 hours.

The present invention is explained in greater details in the description, figures and claims below.

BRIEF DESCRIPTION OF THE DRAWINGS

FIG. 3 describes the permeation of different testosterone formulations through skin in an in vitro system.

DETAILED DESCRIPTION OF THE INVENTION

Figure 1:
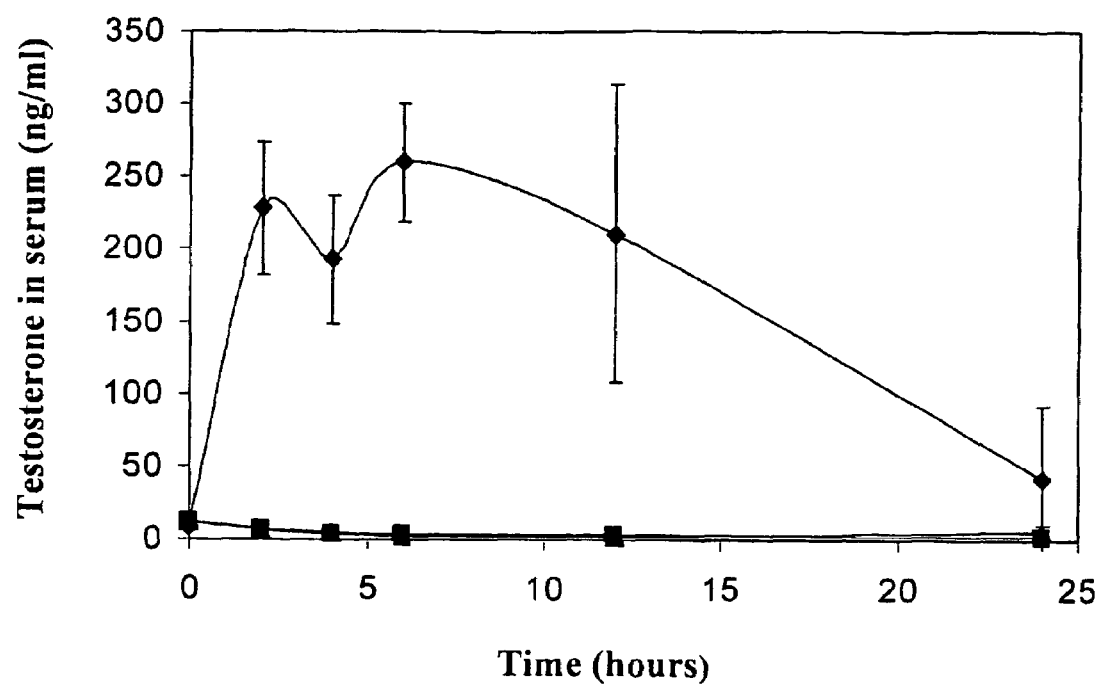
FIG. 1 describes serum concentration of testosterone in non-castrated rats treated with a testosterone-containing patch after the formation of micro-channels by ViaDerm (♦) compared to testosterone level of rats treated with testosterone patch only (■).

The present invention provides a system and methods for an effective transdermal delivery of water-insoluble drugs, particularly of steroids.

The known transdermal patches designed to deliver water insoluble drugs, particularly of steroids, through the stratum corneum have several characteristics:

- The delivery of the molecules occurs through all the area under the patch.
- The interface between the patch and the skin tends to be hydrophobic. This facilitates movement of drug molecules from one hydrophobic matrix (patch) to the other (stratum corneum).
- The patches usually contain permeation enhancers. The purpose of these molecules is to change and disrupt the structure of the stratum corneum, thus elevating the solubility of the drug molecules in the stratum corneum. Enhancers are also responsible for undesired side effects like erythema, edema or pruritis.

The system of the present invention comprises an apparatus for facilitating transdermal delivery of a drug through skin of a subject, said apparatus capable of generating at least one micro-channel in a region of skin of a subject, and a patch comprising a pharmaceutical composition comprising at least one water-insoluble drug and at least one carrier molecule that enhances the solubility of the drug in aqueous solution.

Formation of micro-channels through the stratum corneum into the epidermis eliminates the need of drug molecules to pass through the stratum corneum in order to get into viable tissues. This has several implications:

- The delivery of the molecules occurs mainly through the micro-channels, which occupy less than 1% of the treated skin area.
- There is no need to include penetration enhancers in the formulations, thus improving skin safety.
- Drug molecules should eventually reach the hydrophilic environment of viable tissues underneath the stratum corneum. The hydrophilic micro-channels enable the use of patches comprising drugs already formulated to be water-soluble.

Based on these considerations, the system of the present invention is highly suitable for delivery of drugs formulated in water-soluble formulations, through the micro-channels generated by ablation of the stratum corneum. As a consequence, the system of the present invention does not require the use of permeation enhancers for transdermal drug delivery and is therefore not susceptible to the problems attendant therewith, particularly irritation. Irritation occurs as the skin reacts to topically applied substances, particularly those maintained under occlusion, by blistering or reddening accompanied by unpleasant burning, itching, and stinging sensations. It is desirable to avoid or to keep the number of possibly irritating substances in a transdermal delivery system to a minimum.

The term "micro-channel" as used in the context of the present patent application refers to a pathway generally extending from the surface of the skin through all or a significant part of the stratum corneum, through which molecules can diffuse. In preferred embodiments, the present invention integrates the apparatus and techniques for generating micro-channels by inducing ablation of the stratum corneum by electric current or spark generation applying RF energy disclosed in U.S. Pat. No. 6,148,232 to Avrahami, and continuations thereto (U.S. Pat. Nos. 5,983,135; 6,597,976; 6,611,706; WO 01/085232; WO 02/085451; WO 02/092163), assigned to the assignee of the present application, and incorporated herein in their entirety by reference. However, substantially any method known in the art for generating channels in the skin of a subject may be used (see e.g. U.S. Pat. Nos. 5,885,211, 6,022,316, 6,142,939, 6,173,202, 6,148,232). The terms "micro-pore" and "micro-channels" are used herein interchangeably.

The micro-channels formed by the apparatus of the present invention are hydrophilic having a diameter at the range of 10-100 micron and a depth at 40-300 micron, that facilitate the diffusion of substances through the skin.

According to another embodiment, the present invention provides a medical patch comprising a water insoluble drug. The patch is placed over the treated region in which micro-channels are generated. The patch may comprise any suitable pharmaceutical composition and be of any suitable geometry provided that it is adapted for stable, microbiology-controlled aseptic storage of the drug species prior to its use.

The term "medical patch" and "patch" are used herein interchangeably to define a patch comprising a pharmaceutical composition comprising a water insoluble drug of the invention.

The term "stable" refers herein to a composition that is robust enough to retain at least 80%, preferably 90%, more preferably over 90% of the biological and/or pharmacological activity of the drug for at least 12 months, preferably for at least 24 months, and more preferably for at least 36 months at a temperature of 25° C.

The pharmaceutical composition within the medical patch of the present invention comprises at least one water insoluble drug and at least one carrier molecule that enhances the solubility of the drug in aqueous solution. The unique combination of such hydrophilic pharmaceutical composition with hydrophilic micro-channels disclosed in the present invention provides, for the first time, an efficient transdermal administration of water insoluble drugs without any irritating enhancers.

The term "water insoluble drug" as used herein refers to a compound that typically has solubility in water of less than 0.1-1 mg/ml at room temperature.

According to another embodiment of the present invention, the water-insoluble drug is selected from the group consisting of natural or synthetic anesthetics, analgesics, antagonists, antiadrenergic and antiarrhythmics, antibiotics, anticholinergic and cholinomimetic agents, anticonvulsant agents, antidepressants, anti-epileptics, antifungal and antiviral agents, anti-inflammatory agents, antimuscarinic and muscarinic agents, antineoplastic agents, antipsychotic agents, anxiolytics, hormones, hypnotics, immunosuppressive or immunoactive agents, neuroleptic agents, neuron blocking agents, antihypertensive agents, nutrients, sedatives, steroids, and derivatives thereof.

The term "derivative" includes any chemical derivative of the drug having one or more residues or chemical bonds chemically derivatized by chemical or enzymatic reaction known in the art. Such derivatized molecules include, for example, those molecules in which free hydroxyl groups may be derivatized to form O-acyl or O-alkyl derivatives.

According to yet another embodiment of the present invention, the water insoluble drug is a steroid selected from the group consisting of natural or synthetic androgens, and derivatives thereof. In a currently preferred embodiment, the androgen is testosterone.

According to another embodiment of the present invention, the carrier molecules is selected from the group consisting of α, β and γ cyclodextrin and derivatives thereof. Preferably, the carrier molecule is selected from the group of β cyclodextrins and derivatives thereof. In a currently more preferred embodiment, the carrier molecule is sulfobutyl ether-β-cyclodextrin.

It should be, however, emphasized that the unique system of the present invention provides an efficient transdermal delivery of a water insoluble drug while avoiding the need for permeation enhancers as exemplified herein below. Excluding permeation enhancers from the patch of the present invention overcomes the adverse effects of irritation, itching, erithema, allergic contact dermatitis and the like, known to occur when patches comprising water-insoluble drugs are being used.

According to one currently preferred embodiment, the medical patch of the present invention comprises sulfobutyl ether-α-cyclodextrin as a carrier molecule and testosterone as a water-insoluble steroid.

The formulation of testosterones with a derivative of sulfobutyl ether-β-cyclodextrin ($SBE_7\beta$) was exemplified in U.S. Pat. No. 5,874,418 to Stella et al. incorporated by reference as if fully set forth herein. The present invention shows for the first time that such formulation is effective for transdermal delivery of testosterone (see example 3 herein below). The therapeutic indications in which testosterone is currently being used include man hypogonadism (primary and secondary androgen deficiency) appearing in adults and teenagers, testosterone deficiency in women related to ovaries removal and menopause. Preferred treatment for these indications requires continuous and constant supplement of testosterone. Transdermal application by various types of patches is therefore very attractive. However, as described herein above, the use of such patches is still limited due to their adverse effects, which are eliminated in the system and methods of the present invention, enabling a convenient and efficient transdermal administration of testosterone.

The medical patch may further comprise one or more components known in the art including, but not limited to, soluble polysaccharides, hydrophilic polymers, diluents, colors, preservatives, anti-oxidants, buffer agents, stabilizers, anti-microbial agents, binders, fillers, surfactants, disintegrants, adhesives, and plasticizers. The pharmaceutical composition can be formulated for any suitable patch form, for example a solution, a powder, a gel, a hydrogel, and the like.

Hydrophilic polymers that may be used as adhesives according to the invention include biopolymers or hydrophilic synthetic polymers, derivatives, and combinations thereof. Biopolymers that may be used according to the invention include, but are not limited to, cellulose, chitin, chitosan, alginates, collagens, gelatin, pectin, glycosaminoglycans such as, for example, heparin, chondroitin sulfate, dermatan sulfate, and heparan sulfate, proteoglycans, fibronectins, and laminins.

Hydrophilic synthetic polymers that may be used according to the invention include biodegradable and non-degradable polymers including, but not limited to, polyglycolic acid (PGA) and polylactic acid (PLA) polymers, polyoxypropylene, polyoxyethylene, polyoxyethylene-polyoxypropylene copolymers, polyvinylalcohol, polyethylene glycol, polyvinylpyrrolidone, and polyurethanes. In one currently preferred embodiment, polyvinylpyrrolidone was added to the pharmaceutical composition. In another currently preferred embodiment, Poloxamer 407, a synthetic copolymer of ethylene oxide and propylene oxide was added to the pharmaceutical composition.

According to another preferred embodiment, the medical patch comprises a semi-permeable hydrophilic membrane. The semi-permeable membrane aids in preventing undesirable movement of substances from the skin into the medical patch. For example, testosterone is metabolized to di-hydrotestosterone (DHT) by 5-α-reductase. When generating micro-channels in the skin according to the present invention, fluids coming out of the skin may include this enzyme. In the absence of a semi-permeable membrane, such testosterone metabolism can occur within the patch, destroying the testosterone before it can get into the subject's serum. The semi-permeable membrane also serves as a barrier preventing microorganisms from reaching the pharmaceutical composition within the patch. Preferably, the semi-permeable hydrophilic membrane has a pore size cut-off below 30,000 daltons. The semi-permeable membrane may be fabricated from non-degradable polymers such as polydimethyl siloxane, ethylene-vinyl acetate copolymers, and hydroxylalkyl methacrylates as well as from degradable polymers, among them lactic/glycolic acid copolymers.

According to another embodiment, the patch of the present invention further comprises at least one layer selected from a backing layer, adhesive, and a release liner.

The backing layer functions as the primary structural element of the transdermal system and provides the device with flexibility and, preferably, occlusivity. The material used for the backing layer should be inert and incapable of absorbing drug or any component of the pharmaceutical composition contained within the drug reservoir layer. The backing is preferably comprised of a flexible elastomeric material that serves as a protective covering to prevent loss of drug via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides.

Adhesives, which enable the patch to adhere to the subject's skin, include, but are not limited to, polyurethanes, polyvinyl alcohol, polyacrylic acid, polyacrylates, polyoxyethylene, polyvinylpyrrolidone, poly(hydroxyethyl methacrylate), or copolymers or mixtures thereof.

Application of a patch according to the present invention is accomplished after at least partial removal of any covering or packaging, which protects the patch before use. This exposes the pharmaceutical composition, which may itself have adhesive properties.

According to a further embodiment of the present invention, drug application is accomplished by a medical patch comprising:
 (a) an adhesive cut-out template which is placed on the skin, and through which the cartridge is placed to treat the region of skin exposed through the template, and
 (b) a patch comprising a water-insoluble drug and a carrier, the patch attached to the template, which is to be placed over the treated region of skin. In these applications, after removing a protective layer, the template portion of the medical patch is placed on the skin and secured by the adhesive. An electrode cartridge is then affixed to the apparatus main unit, the user holds the main unit so as to place the cartridge against the region of skin inside the template, and the electrodes are energized to treat the skin. Subsequently, the cartridge is discarded. A protective covering is then removed from the medical patch by pulling on a tab projecting from the covering, so as to concurrently lift and place the medical patch over the treated region of skin. It is noted that the integration of the template and the patch into a single unit assists the user in accurately placing the medical patch onto the treated area of skin. Proper adherence to usage instructions generally ensures avoidance of infections.

According to yet another embodiment, drug application is accomplished by an integrated electrode/medicated pad cartridge, to provide an easy-to-use apparatus also denoted as MicroDerm as disclosed in WO 02/092163, which is assigned to the assignee of the present patent application and incorporated herein by reference. In these applications, the cartridge comprises an electrode array, a controlled unit, and the medicated pad. Accordingly, no template is typically required. The user places the electrodes against the skin and this contact is sufficient to initiate current flow or spark formation within the electrode and the subsequent formation of micro-channels. An adhesive strip, coupled to the bottom of the medicated pad, comes in contact with and sticks to the skin when the electrodes are placed against the skin. A top cover on the medicated pad is coupled to the electrode region of the cartridge, such that as the electrode region fixed to the handle is removed from the skin the top cover is pulled off the medicated pad and the pad is concurrently folded over the treated region of skin. This type of application eliminates the need for the user to touch any parts of the electrode cartridge or the medicated pad, thus substantially reducing or eliminating the likelihood of the user contaminating the apparatus.

According to another embodiment, the system of the present invention comprises an apparatus for facilitating transdermal delivery of a drug through skin of a subject, said apparatus comprises:
 a. an electrode cartridge, optionally removable, comprising at least one electrode, preferably a plurality of electrodes;
 b. a main unit comprising a control unit which is adapted to apply electrical energy to the electrode when the electrode is in vicinity of the skin, typically generating current flow or one or more sparks, enabling ablation of stratum corneum in an area beneath the electrode, thereby generating at least one micro-channel.

According to one embodiment, the control unit of the apparatus comprises circuitry to control the magnitude, frequency, and/or duration of the electrical energy delivered to an electrode, so as to control the current flow or spark generation, and thus the width, depth and shape of the formed micro-channel. Preferably, the electrical energy is at radio frequency.

The pressure obtained while placing the apparatus of the present invention on a subject's skin activates the electrical energy delivered to the electrodes. Such mode of action ensures that activation of electrodes occurs only in a close contact with the skin enabling the desired formation of the micro-channels.

The electrode cartridge is typically discarded after one use, and as such is designed for easy attachment to the main unit and subsequent detachment from the main unit.

To minimize the chance of contamination of the cartridge and its associated electrodes, attachment and detachment of the cartridge is performed without the user physically touching the cartridge. Preferably, cartridges are sealed in a microbiologically controlled cartridge holder, which is opened immediately prior to use, whereupon the main unit is brought in contact with a top surface of the cartridge, so as to engage a mechanism that locks the cartridge to the main unit. A simple means of unlocking and ejecting the cartridge, which does not require the user to touch the cartridge, is also provided.

Optionally the electrode cartridge may further comprise means to mark the region of the skin where micro-channels have been created, such that a medical patch can be precisely placed over the treated region of the skin. It is noted that micro-channel generation according to the apparatus and methods described herein above does not generally leave any visible mark, because even the large number of micro-channels typically generated are not associated with appreciable irritation or edema to the area of ablated skin.

According to the present invention, micro-channels may be formed by the application of current to the skin in order to ablate the stratum corneum by heating the cells. Spark generation, cessation of spark generation, or a specific current level may be used as a form of feedback, which indicates that the desired depth has been reached and current application should be terminated. For these applications, the electrodes are preferably shaped and/or supported in a cartridge that is conducive to facilitate formation of micro-channels in the stratum corneum to the desired depth, but not beyond that depth. Alternatively, the current may be configured so as to form micro-channels in the stratum corneum without the generation of sparks. The resulted micro-channels are uniform in shape and size, as exemplified herein below.

According to one embodiment the present invention incorporates methods and apparatus described in U.S. Pat. No. 6,611,706 to Avrahami and Sohn, entitled, "Monopolar and bipolar current application for transdermal drug delivery and analyte extraction," which is assigned to the assignee of the present patent application and incorporated herein in its entirety by reference. For example, the '936 application describes maintaining the ablating electrodes either in contact with the skin, or up to a distance of about 500 microns therefrom. The '936 application further describes spark-induced ablation of the stratum corneum by applying an electrical field having a frequency between about 10 kHz and 4000 kHz, preferably between about 10 kHz and 500 kHz, more preferably at 100 kHz.

Alternatively or additionally, another embodiments of the present invention incorporate methods and apparatus described in WO 02/085451 entitled, "Handheld apparatus and method for transdermal drug delivery and analyte extraction," which is assigned to the assignee of the present patent application and incorporated herein by reference. Still further alternatively or additionally, another embodiments of the present invention incorporate methods and apparatus described in the above-cited U.S. Pat. No. 6,148,232 to Avrahami, which is assigned to the assignee of the present patent application and incorporated herein by reference.

According to some preferred embodiments of the present invention, the cartridge supports an array of electrodes, preferably closely spaced electrodes, which act together to produce a high micro-channel density in an area of the skin under the cartridge. Typically, however, the overall area of micro-channels generated in the stratum corneum is small compared to the total area covered by the electrode array.

According to further preferred embodiments of the present invention, a concentric electrode set is formed by employing the skin contact surface of the cartridge as a return path for the current passing from the electrode array to the skin. Preferably, the cartridge has a relatively large contact surface area with the skin, resulting in relatively low current densities in the skin near the cartridge, and thus no significant heating or substantial damage to the skin at the contact surface occurs. In proximity to each electrode in the electrode array, by contrast, the high-energy applied field typically induces very rapid heating and ablation of the stratum corneum, creating micro-channels at a precise shape and dimensions.

According to another aspect, the present invention provides a method for facilitating transdermal delivery of a water-insoluble drug comprising: generating at least one micro-channel in a region on the skin of a subject; and affixing a patch to the region of the skin in which the micro-channels are present, the patch comprises a pharmaceutical composition comprising at least one water-insoluble drug and at least one carrier molecule that enhances the solubility of the water insoluble drug in aqueous solution.

According to a further embodiment, the present invention provides a method for facilitating transdermal delivery of a water-insoluble drug comprising:
(i) generating at least one micro-channel in a region on the skin of a subject;
(ii) affixing a patch to the region of the skin in which the micro-channels are present, the patch comprises a pharmaceutical composition comprising at least one water-insoluble drug and at least one carrier molecule that enhances the solubility of the water insoluble drug in aqueous solution; and
(iii) achieving a therapeutically effective blood concentration of the drug for a predetermined period of time.

As defined herein "therapeutically effective blood concentration" means a concentration of the drug, which results in a therapeutic effect.

The method of the invention achieves serum concentration of at least 1 ng/ml of water insoluble drug. Preferably, the serum concentration of at least 1 ng/ml of the water insoluble drug is maintained over a period of at least 12 hours, and more preferably for a period of at least 24 hours.

According to one embodiment, the water insoluble drug is selected from the group consisting of natural or synthetic anesthetics, analgesics, antagonists, antiadrenergic and antiarrhythmics, antibiotics, anticholinergic and cholinomimetic agents, anticonvulsant agents, antidepressants, anti-epileptics, antifungal and antiviral agents, anti-inflammatory agents, antimuscarinic and muscarinic agents, antineoplastic agents, antipsychotic agents, anxiolytics, hormones, hypnotics, immunosuppressive or immunoactive agents, neuroleptic agents, neuron blocking agents, antihypertensive agents, nutrients, sedatives, steroids, and derivatives thereof.

According to another embodiment, the steroid is an androgen. According to a currently preferred embodiment, the androgen is testosterone.

According to a further embodiment, the carrier molecule is selected from the group consisting of α, β and γ cyclodextrins and derivatives thereof.

According to another embodiment, the carrier molecule is selected from the group of β cyclodextrins.

According to yet a currently preferred embodiment, the carrier molecule is sulfobutyl ether-β-cyclodextrin. In a currently more preferred embodiment, the medical patch comprises testosterone and sulfobutyl ether-p-cyclodextrin.

According to a further embodiment, the medical patch may further comprise a hydrophilic polymer. A hydrophilic polymer as disclosed herein below in Example 3 was shown to reduce the release rate of testosterone, and hence to provide a means for slow release of testosterone.

The medical patch can be a part of the apparatus generating the micro-channels, or it can be a separate component from such apparatus; in the latter case the apparatus generating the micro-channels is removed from the skin, and the medical patch is subsequently placed on the ablated skin area.

According to one preferred embodiment, the number of micro-channels generated is adjusted to the amount of water insoluble drug desired to be transferred through the skin.

Having now generally describing the present invention, the same will be more readily understood through reference to the following examples, which are provided by way of illustration and are not intended to be limiting of the present invention.

EXAMPLES

Example 1

Transdermal Delivery of Testosterone in Non-Castrated T-161 Rats

The use of castrated male rats as an animal model for testosterone delivery is well established. However, such model does not represent the actual in vivo conditions, where a testosterone baseline exists. To assess the efficacy of transdermal delivery of testosterone, non-castrated rats were treated with ViaDerm and then administered with a testosterone patch.

Material and Methods:

Animals:
Male rats, 250-300 gr, Sprague Dawley. Control group (no-treatment, non-castrated rats): three rates. Group treated with testosterone: four rats.

Testosterone solution:
Testosterone solution was prepared with sulfobutyl ether-β-cyclodextrin. The preparation procedure was as follows: 400 mg of sulfobutyl ether-β-cyclodextrin (CyDex) were dissolved in water, and then 32 mg of testosterone powder (Fluka chemical) were added to 1 ml of the sulfobutyl ether-β-cyclodextrin/water solution. The mixture was left on a shaker for 24 hours, and then centrifuged for 5 min at 6000 rpm. The supernatant was used for the study.

Patch Preparation and Application:
Silicone (raw material "SIL-K" by Degania Silicone, Israel) was used as a backing liner. 300 μm thick glue was layered on the liner, together with release liner. A square dye was used to punch a hole through the silicone strip. The punched hole was then covered with a 2×2 cm silicone and glued into place using a silicone primer 7701 by Loctite and 4401 glue by Loctite. This created a pouch, sealed by attachment to the body surface, having a volume of 200 μl. Once placed on skin, after assuring that the skin is not damaged, air was withdrawn from the pouch and 200 μl of the testosterone solution prepared as described herein above was injected into the pouch by a 2-ml syringe with 28G needle.

Testosterone Administration:
Rats were treated with ViaDerm and Testosterone as follows:

Under anesthesia, the abdominal fur was clipped and shaved. A pad containing Propyl alcohol was applied on the shaved area, and then the area was air-dried for 30 min. Baseline value of the Trans Epidermal Water Loss (TEWL) was measured. Acceptable range was set to up to 8.5 gr/m²·h.

ViaDerm was applied twice on the shaved skin. The ViaDerm parameters were as follows: burst length—500 μs; starting amplitude—250V; number of bursts—5. After 5 minutes, a second measurement of the TEWL was taken. Acceptable range was set to up to 30 gr/m²·h.

A medical patch containing the testosterone solution (6 mg/200 μl prepared as described herein above) was applied on the skin area treated with ViaDerm. The treated area was bandaged. Blood samples were taken at 0, 2, 4, 6, 12 and 24 h after completion of the patch application, during which time the rats were already not under anesthesia.

In a control group, the rats were shaved, a propyl alcohol pad was applied, and the TEWL was measured.

Blood Sampling:

Each blood sample (0.5 ml) was centrifuged in an Eppendorf test tube at 6,000 rpm for 10 min. Serum was separated by Pasteur pipette into a new 0.5 ml Eppendorf tube and centrifuged again at 6,000 rpm for 5 min. Each serum sample was divided to two and kept at −18° C.

Testosterone Measurements:

Testosterone levels in the serum samples were analyzed using a Testosterone ELISA kit DSL 10-4000.

Results:

Clinical Manifestations.

Twelve to 24 hours post treatment, rats treated with ViaDerm and testosterone developed a black dry secretion around the eyes. The secretion was suspected to be dry blood, which is a symptom suspected to be provoked by stress conditions in rats. Such stress conditions may result from an overdose of testosterone. The intensity of the secretion was assessed and compared on a scale of 1-4: ViaDerm and testosterone treated rats—Rat 1: II; Rat 2: III; Rat 3: II; Rat 4: I. Non-treated rats—No secretion.

Analytical Results:

As shown in FIG. 1, serum concentration of testosterone was significantly higher in rats treated with ViaDerm+testosterone patch than in control rats treated with testosterone patch only. These results also showed that in intact (non castrated) rats a very good penetration profile of the testosterone-sulfobutyl ether-β-cyclodextrin solution is obtained, thus providing a testosterone level higher than the endogenous level for a period longer than 24 hours.

Example 2

Transdermal Delivery of Testosterone in T-178 Pigs

Transdermal testosterone delivery from a commercial patch ("ANDROPATCH®" 5 mg/day, SmithKline Beecham) was compared to transdermal delivery of water-soluble testosterone with or without ViaDerm pretreatment. The application of water-soluble testosterone was performed either in a solution or in a dry form.

Material and Methods:

Animals:

Male pigs, 10-12 Kg, large white, total of 20 pigs.

Air-Dried Patch Preparation and Application:

Silicone sheet (raw material "SIL-K" by Degania Silicone, Israel) was used as a backing liner. 350 μm thick glue was layered on the liner, together with a release liner. A square dye was used to punch a hole through the silicone strip and release liner. A layer of the thick glue was spread on the backing liner sheet. The punched silicone/release liner described above was placed, facing the release liner, on a backing liner.

Two hundred μl of testosterone-sulfobutyl ether-β-cyclodextrin solution (3%, containing 6 mg testosterone as prepared in Example 1) were poured into the cavity formed by the silicone. The solution was spread evenly to form a uniform film and left to dry for at least 12 hours.

Prior to application, the release liner and silicone were removed, rendering the patch ready for use.

Testosterone Administration.

Group 1: Pigs were treated with ANDROPATCH® 5 mg (total amount of 24.3 mg testosterone per patch)—6 pigs.

Group 2: Pigs were treated 6 times with a testosterone-sulfobutyl ether-β-cyclodextrin 3% solution (6 mg/200 μl per application, total of 36 mg testosterone per pig) applied to intact skin—4 pigs.

The treatment steps were as follows: Trunk hair was shaved. A pad containing Propyl alcohol was applied on the shaved area, and the area was air-dried for 30 min. A baseline value of TEWL was measured. Acceptable range was set to up to 8.5 gr/m²·hr.

ViaDerm was applied on the skin without applying a current (placebo application). After 5 minutes, a second measurement of TEWL was taken. Acceptable range was set to a difference of not more than 10% relative to the first TEWL measurement.

A medical patch containing testosterone (prepared as described in Example 1 herein above) was applied on the skin area where ViaDerm was applied. The treated area was bandaged. Blood samples were taken at t=0, 2, 4, 6, 12, 18 and 24 h.

Group 3: Pigs were treated as described for Group 2 except that ViaDerm was applied 5 times at a burst length of 700 μseconds and a starting amplitude of 330V. Six applications of testosterone-sulfobutyl ether-β-cyclodextrin 3% solution (6 mg/200 μl, total of 36 mg per pig; 6 pigs) were performed on the ViaDerm treated skin. Acceptable range for the second TEWL measurement was set to 20 gr/m²·hr.

Group 4: Pigs were treated as described for group 3 except that the medical patch applied contained an air-dried testosterone-sulfobutyl ether-β-cyclodextrin prepared as described herein above.

Six applications of the testosterone—sulfobutyl ether-β-cyclodextrin patches (6 mg/patch, total of 36 mg per pig; 4 pigs) were performed.

Prior to treatments, all pigs went through cannulation of the jugular vein using Arrow CV-50016 central venous catheter.

Blood Sampling:

Blood samples were taken from the jugular catheter at the indicated time points. Each sample (1.5 ml) was centrifuged in an Eppendorf test tube at 6,000 rpm for 10 minutes. Serum was separated by Pasteur pipette into a new 1.5 ml Eppendorf tube and centrifuged again at 6000 rpm for 5 minutes. (In cases were the tube contained fibrin, the sample was centrifuged again at 6000 rpm for 5 minutes). After centrifugation the serum was divided into two 0.5 ml Eppendorf tubes and stored at −18° C.

Testosterone Measurements:

Testosterone levels in the serum samples were analyzed using a Testosterone ELISA kit DSL 10-4000.

Figure 2:
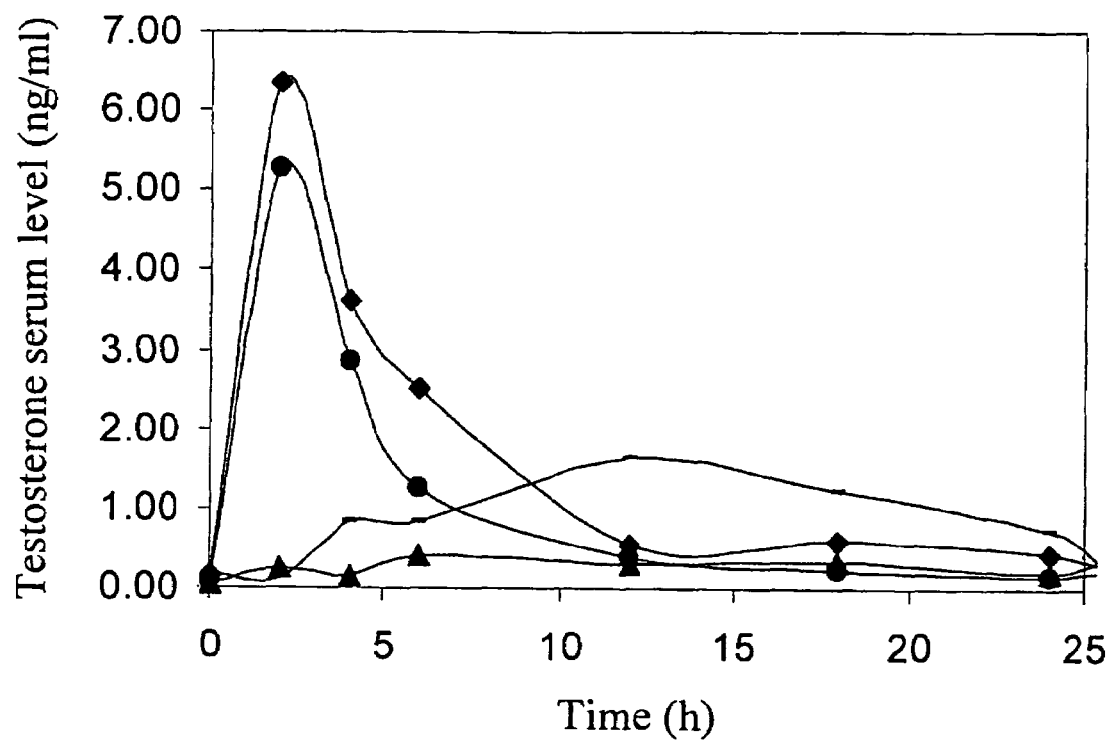
FIG. 2 describes testosterone serum concentration in pigs treated with the following transdermal methods: application of commercial testosterone-containing patch (ANDROPATCH®) on intact skin; application of a patch containing testosterone solution after the formation of micro-channels with ViaDerm; application of air-dried testosterone patch after the formation of micro-channels with ViaDerm; and application of a patch containing testosterone solution without the formation of micro-channels.

Results:

FIG. 2 shows that only a negligible transdermal delivery of water-soluble testosterone was observed. Pretreatment of the skin with ViaDerm enhanced the delivery significantly. The total amounts of testosterone in serum were comparable when the transdermal application was performed by a commercial patch or by the ViaDerm—testosterone system of the present invention, although the pattern of drug delivery was different. These results show that the ViaDerm—testosterone system provides a convenient and patient-friendly transdermal delivery of testosterone.

Example 3

Evaluation of In Vitro Transdermal Delivery of Testosterone Formulated into Hydrogel The term "hydrogel" refers to a three dimensional (3-D) hydrophilic network, which has cross-linked structures and is capable of imbibing large amounts of water or any biological fluid. As a result of absorbing a large quantity of fluid the 3-D network swells to form a substantially water-insoluble hydrogel.

For therapeutic use, it is advantageous to have a slow release testosterone patch, from which the testosterone is released into the subject's serum. In order to achieve a slow release testosterone patch, testosterone was formulated into hydrogel. The rate of testosterone release from the hydrogel patch and its transdermal delivery was examined in vitro by a diffusion cell, using porcine skin.

Two basic formulations of testosterone and hydrogel were prepared, one based on Polyvinylpyrrolidone (PVP) and one on Poloxamer 407 (a synthetic copolymer of ethylene oxide and propylene oxide).

Formulation of Testosterone into Hydrogel Using PVP

The ingredients used for the preparation of testosterone hydrogel with PVP are summarized in Table 1.

TABLE 1

Testosterone formulation using PVP

| Ingredient | Hydrogel 208/1 % Ingredient in solution | Hydrogel 208/2 % Ingredient in solution |
| --- | --- | --- |
| Testosterone | 1 | 1 |
| Sulfobutyl ether-β-cyclodextrin (Captisol) | 12.5 | 12.5 |
| PVP | 18 | 21 |
| Water | 68.5 | 65.5 |

Sulfobutyl ether-β-cyclodextrin was dissolved in water. Testosterone was added to the solution, and the mixture was incubated with shaking for at least 3 h at 600 rpm. The mixture was separated by centrifugation at 2,500 g for 5 min, and the supernatant was used. PVP was slowly added in portions over a period of 1 hour while mixing with a magnetic stirrer, until the solution was clear.

Formulation of Testosterone into Hydrogel Using Poloxamer 407

The ingredients used for the preparation of testosterone hydrogel with Poloxamer 407 are summarized in Table 2.

TABLE 2

Testosterone formulation using Poloxamer 407

| Ingredient | Hydrogel 206/1 % Ingredient in solution | Hydrogel 206/2 % Ingredient in solution |
| --- | --- | --- |
| Testosterone | 1 | 1 |
| Sulfobutyl ether-β-cyclodextrin (Captisol) | 14 | 14 |
| Poloxamer 407 | 24 | 28 |
| Water | 61 | 57 |

Cold water was added to Poloxamer 407. The mixture was mixed vigorously by vortex, and then incubated at −20° C. for at least 30 min. The solid mixture was thawed and then mixed vigorously again. This procedure was repeated until clear solution was obtained. The solution turns into gel upon warming to room temperature. Sulfobutyl ether-β-cyclodextrin (Captisol) was then added to the Poloxamer gel. The gel/captisol mixture was cooled again to a sub-zero temperature in order to liquefy the gel, and the mixture was agitated until all the Captisol was dissolved. The solution turned into gel upon warming to room temperature. Finally, testosterone was added to the clear Captisol-Poloxamer gel. The mixture was cooled again to sub-zero temperature to liquefy the gel and kept at this temperature while stirring to fully dissolve the testosterone. The resulting solution turned into gel upon warming to room temperature. Hydrogel samples containing testosterone were weighed on a backing liner.

Evaluation of In Vitro Transdermal Delivery of Testosterone from Hydrogel

Figure 3A:
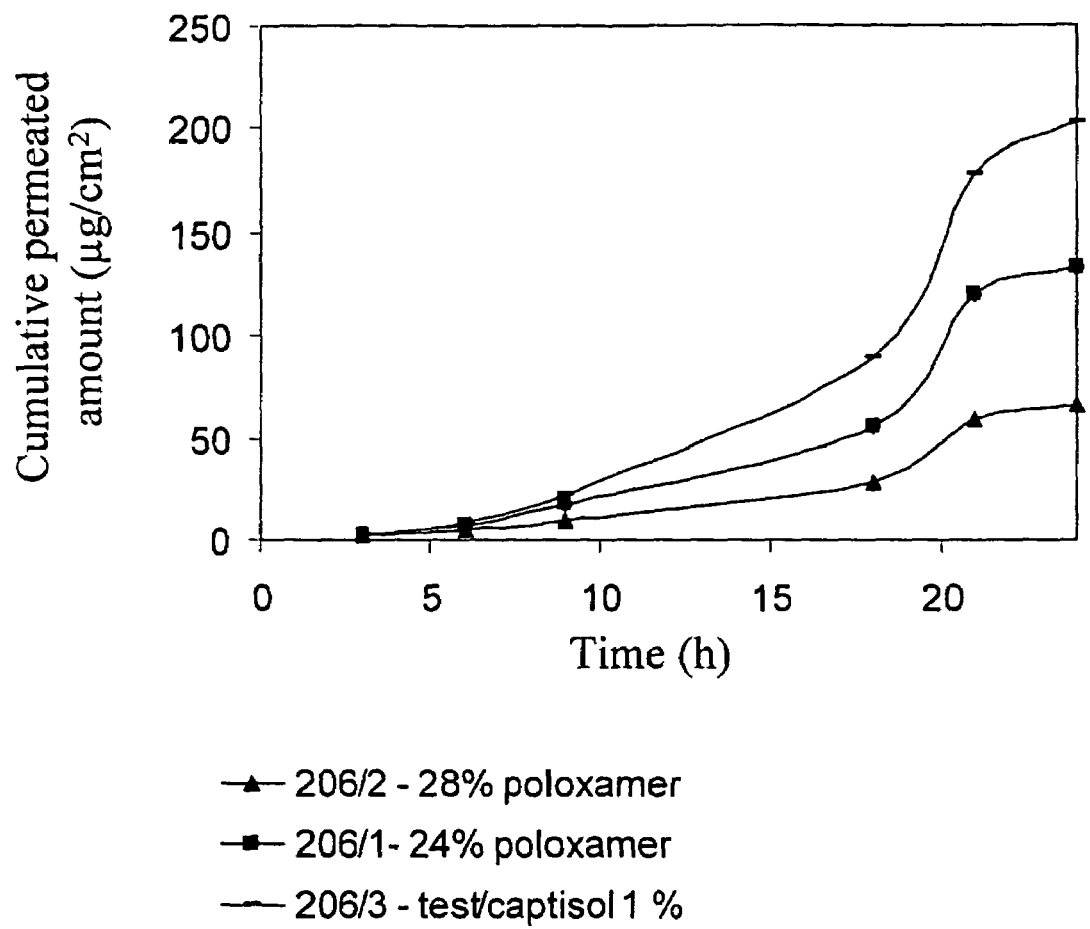
FIG. 3A, testosterone formulation with Poloxamer 407.
Figure 3B:
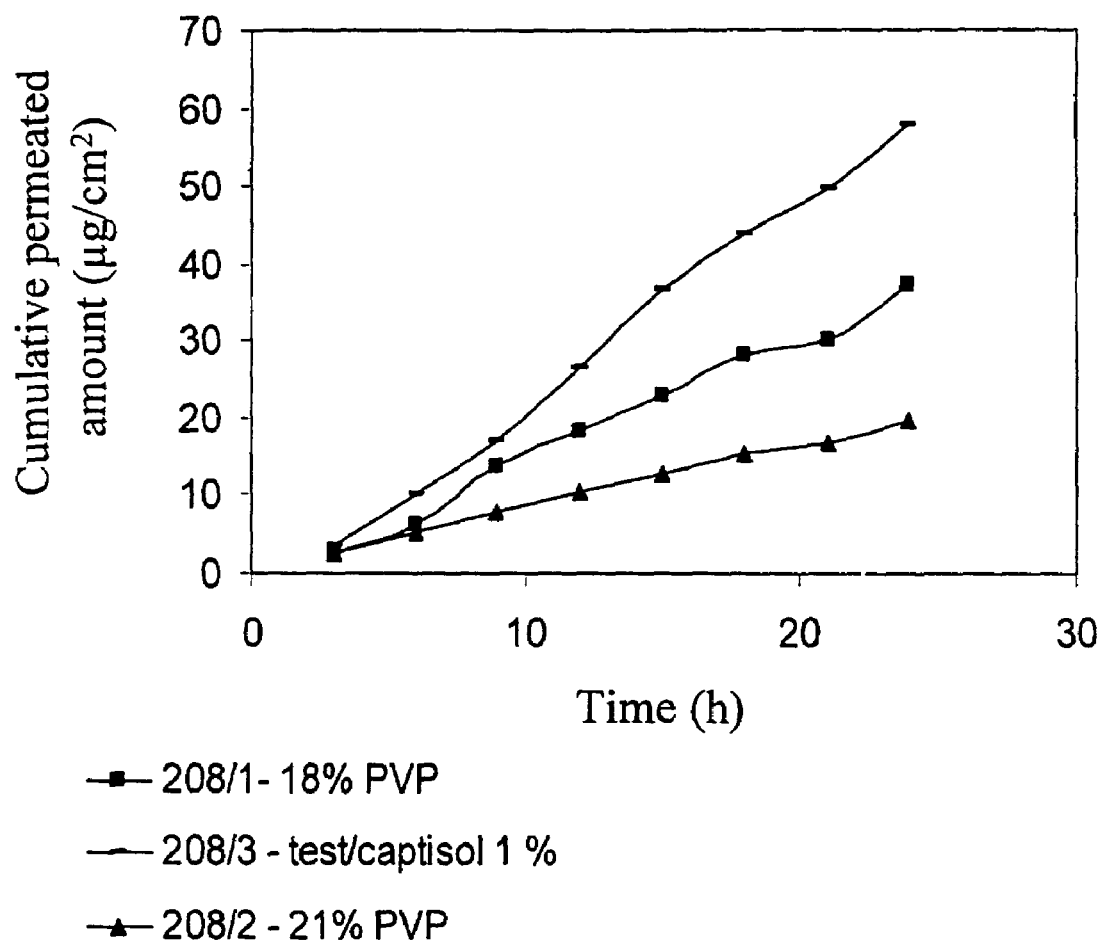
FIG. 3B, testosterone formulation with Polyvinylpyrrolidone (PVP).

A diffusion cell was used to evaluate testosterone release from the hydrogel. Samples of porcine skin were obtained from pig's ear and kept at −20° C. 24 h before use, skin samples were transferred to 4° C., and an hour before use the samples were left uncovered at room temperature. The skin samples were placed across the orifice of the lower portion of a diffusion cell, having a surface of 3.1 cm². The diffusion cell was assembled and the top was covered to prevent the skin from drying. The skin at the diffusion cell was first washed by phosphate buffer saline (PBS) pH 7.2 containing 10% Polyethylene glycol, drawn by a pump from a buffer reservoir at 0.5 ml/min. The temperature around the skin was kept at 33±1° C. by pumping warm water through the diffusion cell jacket. Hydrogel samples containing testosterone were weighed on a backing liner and placed on the porcine skin surface. Buffer was pumped into the diffusion cell at a rate of 16.6 μl/min. The out flow from the cell was collected by a fraction collector at time intervals of 3 h during 24 h. As a control, a reservoir patch containing testosterone solution (1% testosterone-Captisol solution, designated in FIG. 3A and FIG. 3B as 208/3 and 206/3, respectively) was placed on the porcine skin surface in a diffusion cell. As shown in FIG. 3A and FIG. 3B, formulating testosterone into hydrogel promoted slower transdermal delivery through skin. Elevating the hydrogel amount in the testosterone hydrogel formulation reduced the rate of testosterone release.

Example 4

The ViaDerm Apparatus: Specifications and Performance In Vivo

The ViaDerm apparatus that was used to generate microchannels in the pre-clinical and clinical studies described in the above examples is disclosed in U.S. Pat. No. 6,148,232 and in WO 02/085451 and WO 02/092163.

Figure 4:
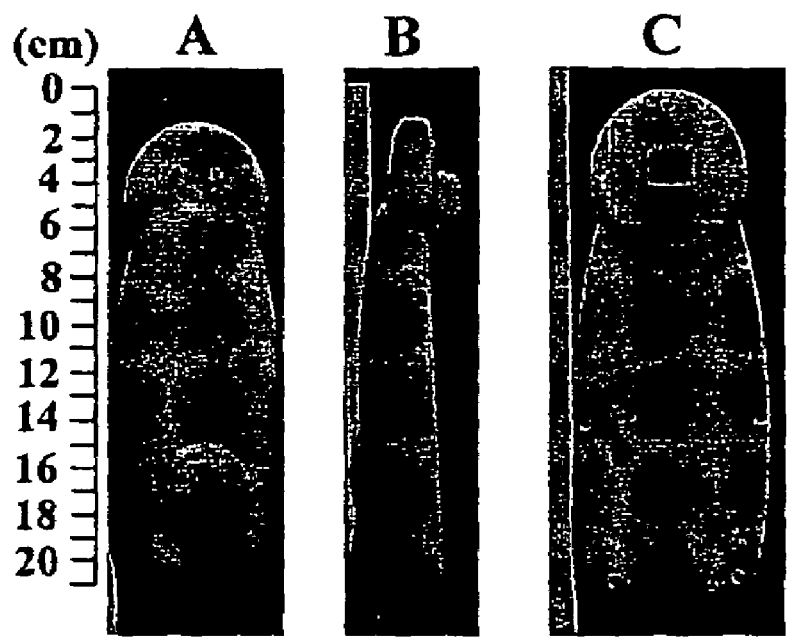
FIG. 4 exhibits top (A), side (B) and bottom (C) views of a ViaDerm apparatus.
Figure 5:
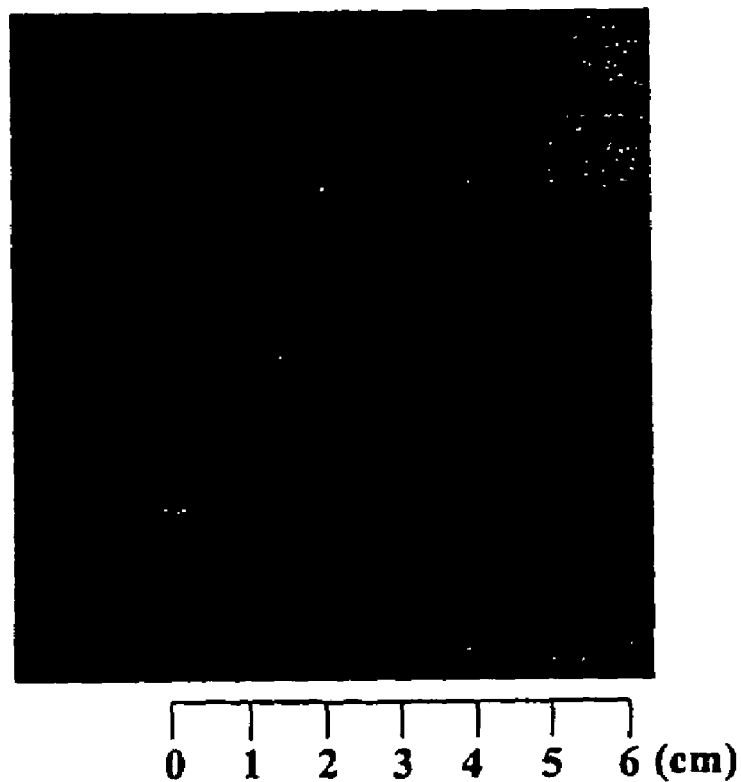
FIG. 5 is a photograph of the electrode cartridge showing the microelectrode array utilized to create micro-channels in the skin, and the same electrode cartridge attached to the main unit of a ViaDerm apparatus.

ViaDerm is comprised of the following:
1. A reusable main unit comprising a control unit, which generates an RF electrical current (FIG. 4).
2. A disposable electrode cartridge (FIG. 5) comprising an array of microelectrodes attached onto the end of the main unit.

Figure 6:
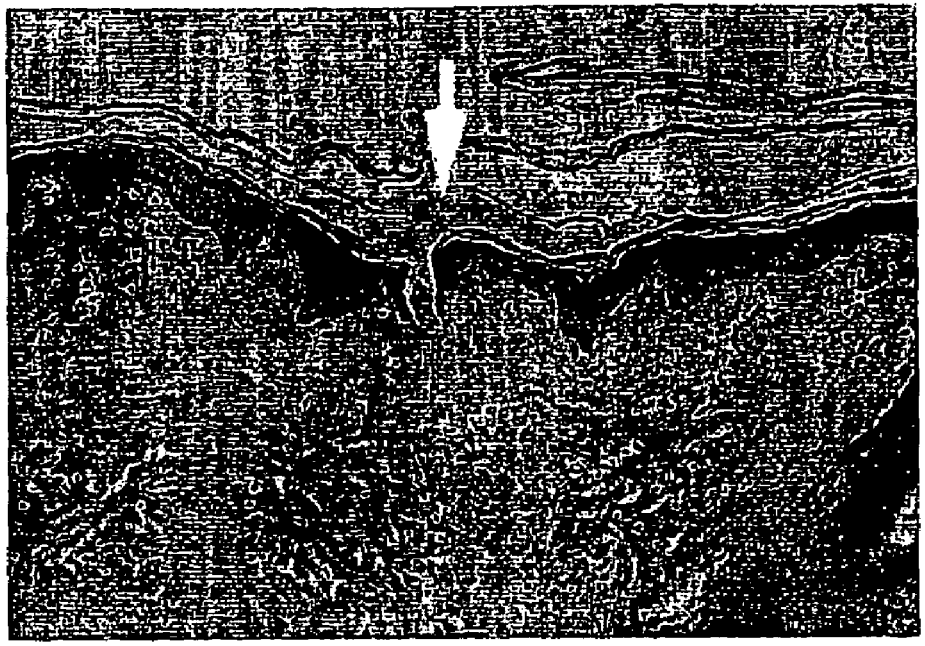
FIG. 6 shows a histological section of porcine skin with micro-channels generated by ViaDerm.

Histological studies of micro-channels generated in a porcine skin by ViaDerm showed that the dimensions of the micro-channels are controllable and precise: each micro-channel was 30 µm in width and 50-100 µm in depth. In porcine skin, as the epidermis depth is about 40 µm, these micro-channels penetrate into the dermis. However in humans, in whom the epidermis depth is about 100 µm, such micro-channels reside within the limits of the epidermis. In addition, the micro-channels were found to be very localized as the skin surrounding the micro-channels maintained its normal structure (FIG. 6).

Figure 7:
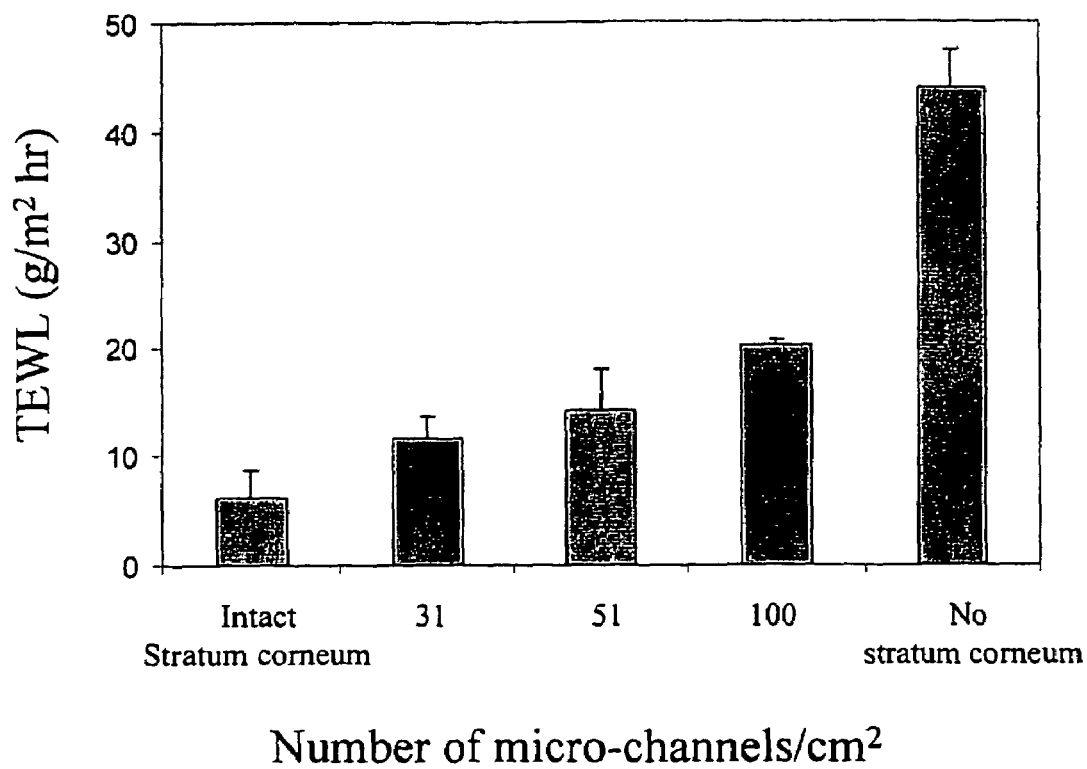
FIG. 7 describes the relationship between Trans Epidermal Water Loss (TEWL) value and the number of micro-channels generated by ViaDerm.
Figure 8:
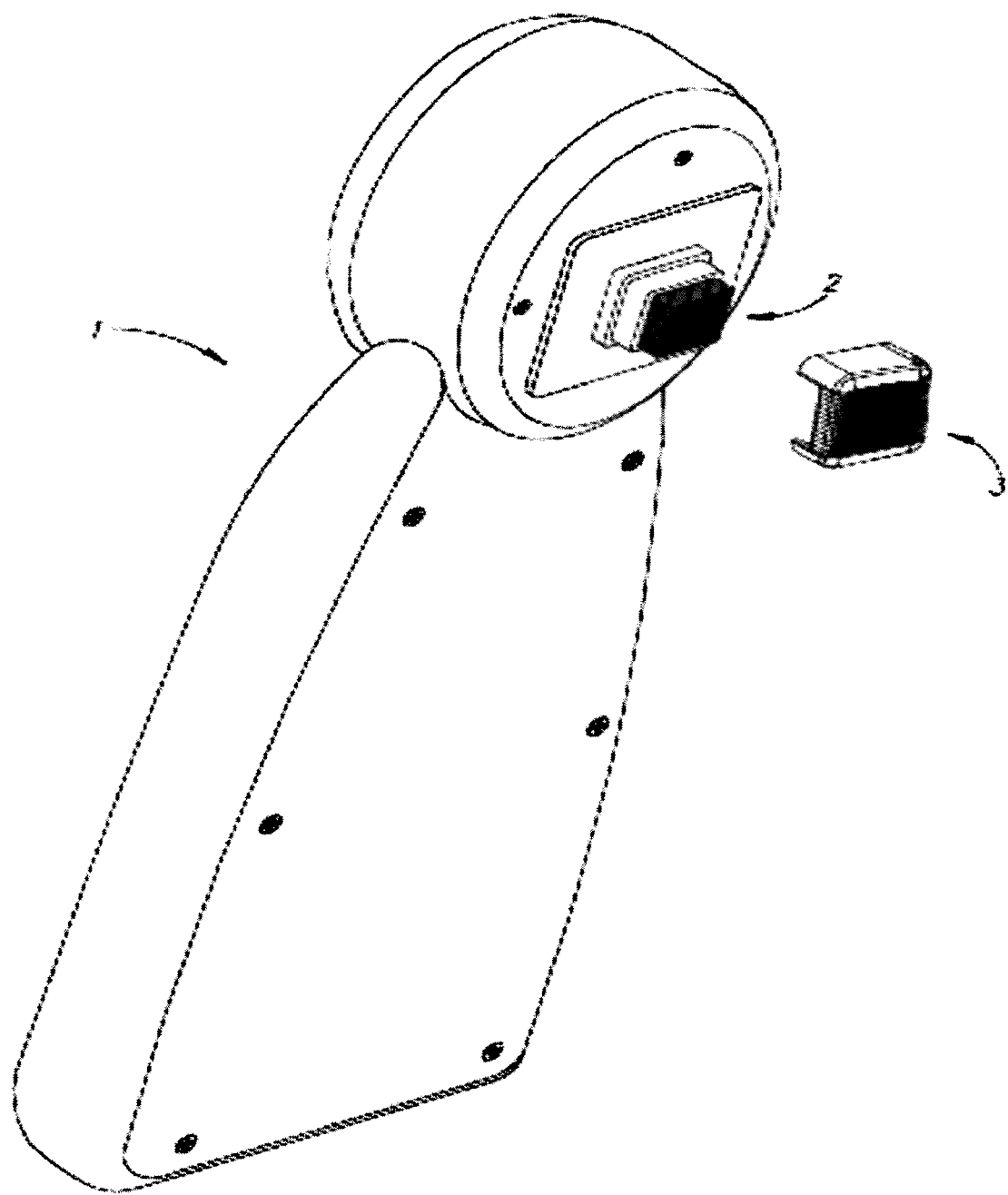
FIG. 8 describes the apparatus of the present invention that includes the main unit (1) containing electric contacts (2) through which electrical energy from the main unit is transferred to the electrode cartridge (3).
Figure 9:
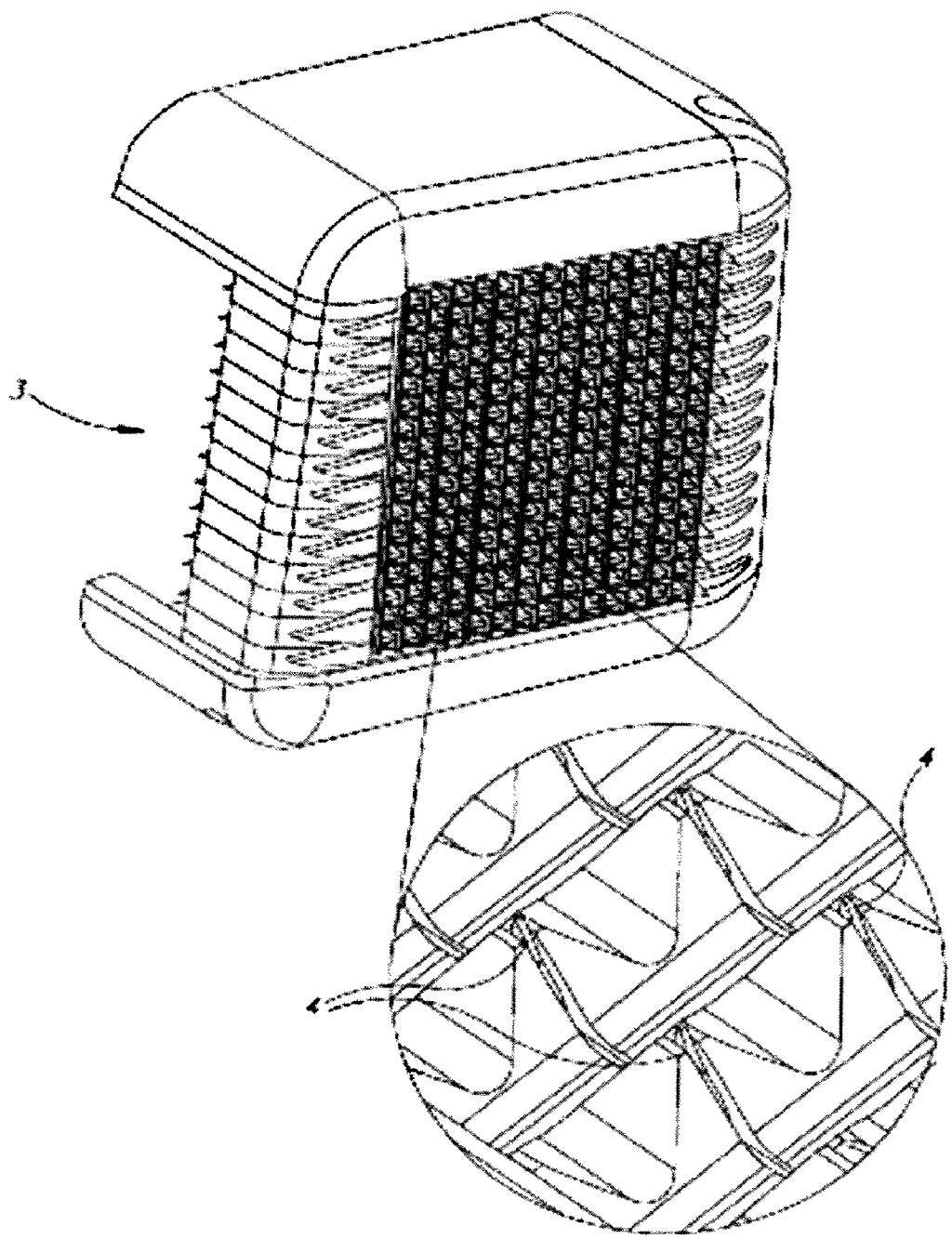
FIG. 9 shows an enlarged region of the electrode cartridge (3) containing electrodes (4).

TEWL was measured in skin sections of porcine ear after generating different numbers of micro-channels (FIG. 7). TEWL linearly increased with increasing number of micro-channels.

Example 5

Clinical Studies of ViaDerm Performance

Materials and Methods

Study Subjects

ViaDerm performance was assessed by a study conducted with twenty healthy, adult volunteers, 10 males and 10 females. The study was conducted at ClinRx a Clinical research organization under Good Laboratory Practice (GLP) standards. Each subject received 10 treatments, in a randomized manner such that a given treatment was applied to different subjects and/or in each subject at different sites.

Treatment Protocol

The treatment sites were the inner arm and hand. Each treatment included the following steps: preparing the skin (cleaning); measuring TEWL ($T_{0-}$) at a treatment site and an adjacent site; placing ViaDerm upon the treatment site and activating the electrodes with controlled RF electrical energy; measuring TEWL immediately at the treatment site and the adjacent site; Scoring for erythema, edema and tolerability ($T_{0+}$), at the treatment site; covering the treatment site with a sterile hydrogel (Vigilon™, The Medical Supply Company Inc., NY, USA) patch; Removing the patch at T=24 hr; measuring TEWL at the treatment site and the adjacent site; Scoring for erythema and edema at the treatment site at T=25 hr and 48 hr.

ViaDerm Performance

Measuring Transdermal Water Loss (TEWL) at a skin site treated with ViaDerm in comparison to an adjacent untreated skin assessed formation of micro-channels. Safety of ViaDerm was evaluated by measuring irritation (erythema and edema) at the treatment site using a scale of zero to eight in accordance with Draize irritation index (Table 3). The response to irritation induced by ViaDerm was assessed by a Cumulative Irritation Index (Table 4). Skin tolerability was studied by measuring pain on a 100 mm Visual Analog Scale (VAS) following ViaDerm treatment.

TABLE 3

Draize irritation index

| | Grade |
|---|---|
| Erythema and Eschar Formation | |
| No erythema | 0 |
| Very slight erythema (barely perceptible) | 1 |
| Well defined erythema | 2 |
| Moderate to severe erythema | 3 |
| Severe erythema (beet redness) to eschar formation preventing grading of erythema | 4 |
| Edema formation | |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond area of exposure) | 4 |
| Total possible score for irritation | 8 |

TABLE 4

Cumulative Irritation Index

| Response category | Mean Score |
|---|---|
| Negligible | 0 to 0.4 |
| Slight | 0.5 to 1.9 |
| Moderate | 2.0 to 4.9 |
| Severe | 5.0 to 8.0 |

Results

Safety Evaluation

Erythema was observed at sites treated with ViaDerm and covered with a patch for 24 hr. This erythema disappeared 24 hr after removal of the patch. Erythema was not observed in non-treated adjacent sites. The maximal mean value of erythema was 0.81 accounting for a very slight erythema according to Table 3. The different application sites exhibited similar irritation scores.

Edema was observed at sites treated with ViaDerm and covered with a patch for 24 hr. This edema disappeared 24 hr after removal of the patch. Edema was not observed in non-treated adjacent sites. The maximal mean value of edema was 0.25 accounting for negligible edema according to Table 3. The different application sites exhibited similar irritation scores.

The maximal mean combined irritation index (erythema and edema) was 0.75 for the ViaDerm treatment sites when occluded and 0.5 for the adjacent non-occluded sites accounting for a minor response.

Tolerability Evaluation

Pain scores were in the range of 0-50 mm. The pain score per subject was an average from 10 ViaDerm applications. The average values (per site of treatment) ranged from 2.1 mm to 7.02 mm. Those values are considered negligible.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A system for transdermal delivery of a water-insoluble drug comprising:
   an apparatus for facilitating transdermal delivery of a drug through skin of a subject, wherein the apparatus comprises:
   a. an electrode cartridge comprising a plurality of electrodes; and
   b. a main unit comprising a control unit which is adapted to apply electrical energy to the electrodes when the electrodes are in vicinity of the skin, enabling ablation of the stratum corneum in an area beneath the electrodes, thereby generating a plurality of hydrophilic micro-channels; and
   a patch adapted to be applied to the area on the skin after the plurality of hydrophilic micro-channels is generated, wherein the patch comprises a pharmaceutical composition comprising at least one water-insoluble drug and at least one carrier molecule that enhances the solubility of the drug in an aqueous solution of fluid coming out of the skin when said plurality of hydrophilic micro-channels is generated, the pharmaceutical composition is devoid of a permeation enhancer.

2. The system according to claim 1, wherein the cartridge is removable.

3. The system according to claim 1, wherein the electrical energy applied to the electrode is of radio frequency.

4. The system according to claim 1, wherein the water insoluble drug is selected from the group consisting of natural or synthetic anesthetics, analgesics, antagonists, antiadrenergics, antiarrhythmics, antibiotics, anticholinergic and cholinomimetic agents, anticonvulsant agents, antidepressants, anti-epileptics, antifungal and antiviral agents, anti-inflammatory agents, antimuscarinic and muscarinic agents, antineoplastic agents, antipsychotic agents, anxiolytics, hormones, hypnotics, immunosuppressive or immunoactive agents, neuroleptic agents, neuron blocking agents, antihypertensive agents, nutrients, sedatives, steroids, and derivatives thereof.

5. The system according to claim 4, wherein the steroid is testosterone.

6. The system according to claim 1, wherein the carrier molecule is selected from the group consisting of α, β and γ cyclodextrins and derivatives thereof.

7. The system according to claim 1, wherein the water-insoluble drug is testosterone and the carrier molecule is selected from the group consisting of sulfobutyl ether-β-cyclodextrin and hydroxypropyl-β-cyclodextrin.

8. The system according to claim 1, wherein the pharmaceutical composition further comprising at least one hydrophilic polymer.

9. The system according to claim 8, wherein the hydrophilic polymer is selected from the group consisting of polyglycolic acid and polylactic acid polymers, polyoxypropylene, polyoxyethylene, polyoxyethylene-polyoxypropylene copolymers, polyvinylalcohol, polyethylene glycol, polyvinylpyrrolidone, and polyurethanes.

10. The system according to claim 8, wherein the hydrophilic polymer is selected from the group consisting of polyoxyethylene-polyoxypropylene copolymers and polyvinylpyrrolidone.

11. The system according to claim 1, wherein the pharmaceutical composition is formulated in a form selected from the group consisting of a powder, a solution, a gel, and a hydrogel.

12. The system according to claim 1, wherein the pharmaceutical composition further comprises at least one component selected from the group consisting of preservatives, antioxidants, anti-microbial agents, soluble polysaccharides, adhesives, and diluents.

13. The system according to claim 1, wherein the patch further comprises a layer selected from the group consisting of a backing layer, adhesive, and a release liner.

14. A method for transdermal administration of a water-insoluble drug comprising:
   (i) generating a plurality of hydrophilic micro-channels in an area of skin of a subject by an apparatus comprising:
   a. an electrode cartridge comprising a plurality of electrodes; and
   b. a main unit comprising a control unit which is adapted to apply electrical energy to the electrodes when the electrodes are in vicinity of the skin, enabling ablation of the stratum corneum in the area beneath the electrodes, thereby generating a plurality of hydrophilic micro-channels; and
   (ii) affixing a patch to said area of skin in which the plurality of hydrophilic micro-channels is present, wherein the patch comprises a pharmaceutical composition comprising at least one water-insoluble drug and at least one carrier molecule that enhances the solubility of the drug in an aqueous solution of fluids coming out of the skin when said plurality of hydrophilic micro-channels is generated, the pharmaceutical composition is devoid of a permeation enhancer.

15. The method according to claim 14, wherein the water insoluble drug is selected from the group consisting of natural or synthetic anesthetics, analgesics, antagonists, antiadrenergic and antiarrhythmics, antibiotics, anticholinergic and cholinomimetic agents, anticonvulsant agents, antidepressants, anti-epileptics, antifungal and antiviral agents, anti-inflammatory agents, antimuscarinic and muscarinic agents, antineoplastic agents, antipsychotic agents, anxiolytics, hormones, hypnotics, immunosuppressive or immunoactive agents, neuroleptic agents, neuron blocking agents, antihypertensive agents, nutrients, sedatives, steroids, and derivatives thereof.

16. The method according to claim 15, wherein the steroid is testosterone.

17. The method according to claim 14, wherein the carrier molecule is selected from the group consisting of α, β and γ cyclodextrins and derivatives thereof.

18. The method according to claim 14, wherein the water-insoluble drug is testosterone and the carrier molecule is selected from the group consisting of sulfobutyl ether-β-cyclodextrin and hydroxypropyl-β-cyclodextrin.

19. The method according to claim 14, wherein the pharmaceutical composition further comprising at least one hydrophilic polymer.

20. The method according to claim 19, wherein the hydrophilic polymer is selected from the group consisting of polyglycolic acid and polylactic acid polymers, polyoxypropylene, polyoxyethylene, polyoxyethylene-polyoxypropylene copolymers, polyvinylalcohol, polyethylene glycol, polyvinylpyrrolidone, and polyurethanes.

21. The method according to claim 19, wherein the hydrophilic polymer is selected from the group consisting of polyoxyethylene-polyoxypropylene copolymers and polyvinylpyrrolidone.

22. The method according to claim 14, wherein the pharmaceutical composition is formulated in a form selected from the group consisting of a powder, a solution, a gel, and a hydrogel.

23. The method according to claim 14, wherein the pharmaceutical composition further comprises at least one component selected from the group consisting of preservatives, anti-oxidants, anti-microbial agents, soluble polysaccharides, adhesives, and diluents.

24. The method according to claim 14, wherein the patch further comprises a layer selected from the group consisting of a backing layer, adhesive, and a release liner.

25. The method according to claim 14, wherein the electrode cartridge is removable.

26. The method according to claim 14, wherein the electrical energy applied to the electrode is of radio frequency.

27. A method for transdermal administration of a water-insoluble drug comprising:
  (i) generating a plurality of hydrophilic micro-channels in an area of skin of a subject by an apparatus comprising:
    a. an electrode cartridge comprising a plurality of electrodes; and
    b. a main unit comprising a control unit which is adapted to apply electrical energy to the electrodes when the electrodes are in vicinity of the skin, enabling ablation of the stratum corneum in the area beneath the electrodes, thereby generating a plurality of hydrophilic micro-channels; and
  (ii) affixing a patch to said area of skin in which the plurality of hydrophilic micro-channels is present, wherein the patch comprises a pharmaceutical composition comprising at least one water-insoluble drug and at least one carrier molecule that enhances the solubility of the drug in an aqueous solution of fluids coming out of the skin when said plurality of hydrophilic micro-channels is generated, said pharmaceutical composition is devoid of a permeation enhancer; and
  (iii) achieving a therapeutic blood concentration of the drug.

28. The method according to claim 27, wherein the water insoluble drug is selected from the group consisting of natural or synthetic anesthetics, analgesics, antagonists, antiadrenergics, antiarrhythmics, antibiotics, anticholinergic and cholinomimetic agents, anticonvulsant agents, antidepressants, anti-epileptics, antifungal and antiviral agents, anti-inflammatory agents, antimuscarinic and muscarinic agents, antineoplastic agents, antipsychotic agents, anxiolytics, hormones, hypnotics, immunosuppressive or immunoactive agents, neuroleptic agents, neuron blocking agents, antihypertensive agents, nutrients, sedatives, steroids, and derivatives thereof.

29. The method according to claim 28, wherein the steroid is testosterone.

30. The method according to claim 27, wherein the carrier molecule is selected from the group consisting of $\alpha$, $\beta$ and $\gamma$ cyclodextrins and derivatives thereof.

31. The method according to claim 27, wherein the water-insoluble drug is testosterone and the carrier molecule is selected from the group consisting of sulfobutyl ether-$\beta$-cyclodextrin and hydroxypropyl-$\beta$-cyclodextrin.

32. The method according to claim 27, wherein the pharmaceutical composition further comprises at least one hydrophilic polymer.

33. The method according to claim 32, wherein the hydrophilic polymer is selected from the group consisting of polyglycolic acid and polylactic acid polymers, polyoxypropylene, polyoxyethylene, polyoxyethylene-polyoxypropylene copolymers, polyvinylalcohol, polyethylene glycol, polyvinylpyrrolidone, and polyurethanes.

34. The method according to claim 32, wherein the hydrophilic polymer is selected from the group consisting of polyoxyethylene-polyoxypropylene copolymers and polyvinylpyrrolidone.

35. The method according to claim 27, wherein the pharmaceutical composition is formulated in a form selected from the group consisting of a powder, a solution, a gel, and a hydrogel.

36. The method according to claim 27, wherein the pharmaceutical composition further comprises at least one component selected from the group consisting of preservatives, anti-oxidants, anti-microbial agents, soluble polysaccharides, adhesives, and diluents.

37. The method according to claim 27, wherein the patch further comprises a layer selected from the group consisting of a backing layer, adhesive, and a release liner.

38. The method according to claim 27, wherein the electrode cartridge is removable.

39. The method according to claim 27, wherein the electrical energy applied to the electrode is of radio frequency.

* * * * *

UNITED STATES PATENT AND TRADEMARK OFFICE
CERTIFICATE OF CORRECTION

PATENT NO. : 7,395,111 B2
APPLICATION NO. : 11/116056
DATED : July 1, 2008
INVENTOR(S) : Levin et al.

It is certified that error appears in the above-identified patent and that said Letters Patent is hereby corrected as shown below:

Column 21:
Line 44 (claim 3, line 2), change "electrode" to -- electrodes --.

Column 22:
Lines 46-47 (claim 15, lines 3-4), change "antiadrenergic" to -- antiadrenergies, --; and before "antiarrhythmics," delete "and".
Line 66 (claim 19, line 2), change "comprising" to -- comprises --.

Column 23:
Line 39 (claim 27, line 12), after "micro-channels," delete "and".

Signed and Sealed this

Thirtieth Day of September, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,395,111 B2 | Page 1 of 1 |
| APPLICATION NO. | : 11/116056 | |
| DATED | : July 1, 2008 | |
| INVENTOR(S) | : Levin et al. | |

It is certified that error appears in the above-identified patent and that said Letters Patent is hereby corrected as shown below:

<u>Column 21</u>:
Line 44 (claim 3, line 2), change "electrode" to -- electrodes --.

<u>Column 22</u>:
Lines 46-47 (claim 15, lines 3-4), change "antiadrenergic" to -- antiadrenergies, --; and before "antiarrhythmics," delete "and".
Line 66 (claim 19, line 2), change "comprising" to -- comprises --.

<u>Column 23</u>:
Line 39 (claim 27, line 12), after "micro-channels," delete "and".

This certificate supersedes the Certificate of Correction issued September 30, 2008.

Signed and Sealed this

Third Day of February, 2009

JOHN DOLL
*Acting Director of the United States Patent and Trademark Office*

UNITED STATES PATENT AND TRADEMARK OFFICE
CERTIFICATE OF CORRECTION

PATENT NO.       : 7,395,111 B2                                            Page 1 of 1
APPLICATION NO.  : 11/116056
DATED            : July 1, 2008
INVENTOR(S)      : Levin et al.

It is certified that error appears in the above-identified patent and that said Letters Patent is hereby corrected as shown below:

<u>Column 21</u>:
Line 44 (claim 3, line 2), change "electrode" to -- electrodes --.

<u>Column 22</u>:
Lines 46-47 (claim 15, lines 3-4), change "antiadrenergic" to -- antiadrenergics, --; and before "antiarrhythmics," delete "and".
Line 66 (claim 19, line 2), change "comprising" to -- comprises --.

<u>Column 23</u>:
Line 39 (claim 27, line 12), after "micro-channels," delete "and".

This certificate supersedes the Certificates of Correction issued September 30, 2008 and February 3, 2009.

Signed and Sealed this

Twenty-sixth Day of May, 2009

JOHN DOLL
*Acting Director of the United States Patent and Trademark Office*